United States Patent [19]
Tsao

[11] 4,243,650
[45] Jan. 6, 1981

[54] HEAT AND VOLATIZED SALT RECOVERY FROM REACTION EFFLUENT

[75] Inventor: Utah Tsao, Jersey City, N.J.

[73] Assignee: The Lummus Company, Bloomfield, N.J.

[21] Appl. No.: 48,147

[22] Filed: Jun. 13, 1979

Related U.S. Application Data

[63] Continuation-in-part of Ser. No. 870,351, Jan. 18, 1978, abandoned, and Ser. No. 25,278, Mar. 29, 1979, abandoned.

[51] Int. Cl.³ .................. B01D 5/00; C07C 17/00
[52] U.S. Cl. .................. 423/659; 423/210.5; 423/240; 423/493; 423/DIG. 12; 55/71; 55/72; 55/77; 55/82; 570/223; 570/224; 570/243
[58] Field of Search .................. 423/210, 210.5, 240, 423/659, 493, DIG. 12; 55/71, 72, 73, 77, 82; 260/654 A, 654 R, 659 A, 659 R, 662 A, 662 R, DIG. 42, 652 P, 656 R

[56] References Cited

U.S. PATENT DOCUMENTS

| | | |
|---|---|---|
| 2,407,828 | 9/1946 | Gorin .................. 260/659 R |
| 2,447,323 | 8/1948 | Fontana .................. 260/659 A |
| 2,498,546 | 2/1950 | Gorin .................. 260/DIG. 42 |
| 2,498,552 | 2/1950 | Kilgren et al. .................. 260/DIG. 42 |
| 2,580,635 | 1/1952 | Winter, Jr. .................. 55/72 X |
| 2,897,918 | 8/1959 | Schlotthauer et al. .................. 55/72 X |
| 3,443,360 | 5/1969 | Reeves .................. 55/71 |
| 4,120,668 | 10/1978 | Fraley .................. 423/210.5 X |

Primary Examiner—Earl C. Thomas
Attorney, Agent, or Firm—Louis E. Marn; Elliot M. Olstein

[57] ABSTRACT

A reaction effluent containing vaporized salt withdrawn from a reaction zone, such as a molten salt reaction zone, is contacted with solid particles to cool the gas and condense vaporized salt onto the particles. Such contacting may be effected in either a fluidized bed of solids or in a dilute phase transport contact zone. Heat is recovered either by indirect heat transfer in the fluidized bed or by separating the solid particles and introduction thereof into a fluidized bed cooled by indirect heat transfer. Solid salt is attrited from the particles during contacting with the reaction gas and fluidizing gas, with such solid salts being returned to the reaction zone.

27 Claims, 3 Drawing Figures

HEAT AND VOLATIZED SALT RECOVERY FROM REACTION EFFLUENT

This application is a continuation in part of U.S. application Ser. No. 870,351 filed on Jan. 18, 1978, and a continuation in part of U.S. application Ser. No. 25,278 filed on Mar. 29, 1979 both now abandoned.

This invention releates to recovery of heat and vaporzed salt from a reaction effluent which contains vaporzed salt.

In many processes, the reaction effluent withdrawn from a reaction zone includes a vaporized salt derived from the use of such a salt in the reaction zone. Thus, for example, such salt may be employed in a reaction zone in molten form, and the reaction effluent withdrawn from the reaction zone includes vaporized portions of such molten salt. Similarly, in some cases, such vaporized salt may also be present in a reaction effluent recovered from a reaction zone employing the salt in solid form or on a solid support. Such effluent gases also include heat energy values which must be effectively recovered from the effluent to improve the overall economics of the process.

Thus, for example, a molten salt mixture containing the higher and lower valent chlorides of a multivalent metal, such as a mixture of cuprous and cupric chloride, is employed for the production of a chlorinated hydrocarbon. In such a process, a hydrocarbon, such as ethane and/or ethylene, is contacted with the salt mixture to produce chlorinated product. In such a process, a small amount of the molten salt is volatized into the gaseous effluent stream, and such volatized salt is generally removed from the effluent stream by direct contact with an aqueous hydrogen chloride stream.

There is a need for a new and improved process for effectively recovering both heat and salt present in a reaction effluent which contains vaporized salt.

In accordance with one aspect of the present invention, there is provided a new and improved process for recovering heat from a reaction effluent containing a vaporized salt, which also provides for recovery of such vaporized salt. More particularly, in accordance with one aspect of the present invention, a reaction effluent withdrawn from a reaction zone, which contains vaporized salt, is contacted with solid particles which are at a temperature at which the volatized salt is condensed from the effluent onto the solid particles to thereby separate volatized salt from the stream. Such contacting also results in a cooling of the effluent and a heating of the solids, with heat subsequently being recovered from the solids by indirect heat transfer.

In accordance with one aspect of the present invention, the effluent is contacted with the solid particles in a bed of the particles, preferably as a fluidized bed. In accordance with another aspect of the present invention, the solid particles contact the effluent in a dilute phase transport contact zone, with the solid particles in both cases being at a temperature at which vaporized salt condenses from the effluent onto the solid particles. As a result of such contact, the effluent gas is cooled, and vaporized salt is separated from the gas by condensation onto the solid particles.

In accordance with the aspect of the present invention wherein the effluent gas is contacted with the solid particles in a fluidized bed, the bed of particles is conveniently maintained at the required temperature by indirect heat transfer; e.g., by employing a heat exchange coil within the bed or by employing a jacketed vessel. A wide variety of heat transfer fluids may be employed for maintaining the bed of particles at the desired temperature, with such heat transfer fluid preferably being water to effect generation of steam at a medium pressure. Thus, by the use of a cooling coil containing water, heat present in the gaseous effluent may be conveniently recovered by the generation of steam.

In the embodiment of the invention wherein solid particles are added to the gaseous effluent and contacting is effected in a dilute phase transport contact zone, the solid particles are separated from the gaseous effluent, followed by cooling thereof for reuse in the contacting with the gaseous effluent. The particles may be cooled by indirect heat transfer; e.g., by cooling the particles in a separate vessel by the use of a heat exchange coil in a bed thereof or by employing a jacketed vessel. Heat may be suitably recovered; e.g. as by the generation of steam. The particles are preferably maintained as a fluidized bed during such indirect cooling.

In accordance with a preferred embodiment of the present invention, salt present on the solid particles is attrited from such particles into the effluent gas, and in the case where the particles are separated from the gas and cooled in a fluidized bed, salt is also attrited into the fluidizing gas. Such attrited salt particles are eventually returned to the reaction system, whereby salt originally carried from then reaction system into the reaction effluent is recycled thereto. In accordance with a particularly preferred embodiment, solid salt is attrited from the solid particles in an equilibrium relationship with the condensation of vaporized salt onto the solid particles, whereby there is essentially no buildup of salt on the particles. In some cases, where such equilibrium is not reached, it may be necessary to periodically treat overrun particles to remove deposited salt. Such coated salt may be removed by any one of a wide variety of procedures. Thus, for example, the particles may be washed with water or other suitable liquid compatible with the reaction system to permit return of the salt to the reaction system.

The solid salt particles contained in the effluent gas and/or fluidizing gas may be recovered for recycle to the reaction system by any one of a wide variety of procedures. Thus, for example, such solid particles may be recovered by filtration.

In accordance with a particularly preferred embodiment, in the case where the solid particles are separately cooled in a fluidizing bed by use of a fluidizing gas, such fluidizing gas may be a gas which is to be introduced into the reaction system, either as fresh feed or a recycle gas, whereby the attrited salt particles may be introduced into the reaction system in such feed or recycle gas.

In accordance with another embodiment of the present invention, the solid particles which are employed for contacting the gas to condense vaporized salt may be either the metal or a metal salt which corresponds to the vaporized salt, whereby solid particles, now coated with condensed vaporized salt may be directly returned to the reaction system. Thus, for example, if the reaction system employs molten copper chlorides, which include; for example, potassium chloride as a melting point depressant, the solid particles may be copper, a copper chloride or potassium chloride.

In accordance with the most preferred embodiment, a reaction effluent withdrawn from a reaction zone, which contains vaporized salt, is contacted with solid particles in a dilute phase transport contact zone, with the solid particles being at a temperature at which vaporized salt condenses from the effluent onto the solid particles. As a result of such contact, the effluent gas is cooled, and vaporized salt is separated from the gas by condensation onto the solid particles.

Heat is then recovered from solid particles separated from the effluent gas in a fluidized bed contacting zone wherein the solid particles, in a fluidized state, are cooled by indirect heat transfer with a suitable heat transfer fluid, such as water, to thereby effectively recover a portion of the heat from the gaseous reaction effluent. The solid particles are maintained in a fluidized state by use of at least a portion of the feed (fresh feed or recycle feed) for the reaction system, in gaseous form, with such fluidizing gas being heated by contact with the solid particles. In addition, salt present on the solid particles is attrited from such particles into the feed gas. The feed gas, which has been heated, and which now contains solid fines of the salt may then be introduced into the reaction system, whereby salt originally carried from the reaction system in the reaction effluent is recycled to the reaction zone.

Cooled solid particles withdrawn from the fluidized bed are then reused for cooling the effluent gas and condensing vaporized salt therefrom.

After separation of the solid particles from the effluent gas, the effluent gas is then further cooled by indirect heat transfer with a suitable heat transfer fluid, such as, for example, water, in order to recover further heat therefrom. The effluent gas may contain some of the salt as solid fines as a result of attrition of such solid salt from the solid particles; however, such solid particles do not adversely affect such further heat recovery.

The effluent gas, after such further heat recovery, may then be processed in a suitable recovery system. Such recovery system should preferably provide for recovery of any solid salt fines which are present in the reaction effluent. Such recovery may be effected by any one of a wide variety of procedures. In accordance with a preferred procedure, such salt fines are recovered from the effluent gas by use of a liquid recycle stream to an appropriate reaction zone employing the salt.

The solid particles which are employed for condensing the vaporized salt from the gaseous effluent may be any one of a wide variety of particles which do not adversely affect the components in the gaseous stream. As representative examples of such particles, there may be mentioned: sand, glass beads, ceramics, metals, metal salts and in particular metals and metal salts which correspond to those used in the reaction zone.

Although the invention has general applicability to any one of a wide variety of processes wherein an effluent stream from a reaction system contains volatized salt, the present invention has particular applicability to a reaction system which employs a salt in molten form. Such reaction systems are generally known in the art, and no particular details in this respect are needed for complete understanding of the present invention.

In accordance with a particularly preferred embodiment, the present invention is employed in a reaction system which employs a molten salt which contains the higher and lower valent forms of a chloride of a multivalent metal; i.e., a metal having more than one positive valent state, such as manganese, iron, copper, cobalt, and chromium, preferably copper. In the case of higher melting multivalent metal chlorides, such as copper chlorides, the metal salt melting point depressant, which is non-volatile and resistant to the reaction of oxygen at the processing conditions, such as a chloride of a univalent metal; i.e., a metal having only one positive valent state, is added to the multivalent metal chloride to form a molten salt mixture having a reduced melting point. The metal chlorides employed as melting point depressants are preferably alkali metal chlorides, such as potassium and lithium chloride, in particular, but it is to be understood that other metal chlorides and mixtures thereof, such as the heavy metal chlorides; i.e., heavier than copper, of groups I, II, III and IV of the Periodic Table; e.g., zinc, silver and thallium chloride may also be employed. In general, the metal chloride melting point depressant is added in an amount sufficient to maintain the salt mixture as a melt at the reaction temperatures, and is generally added in an amount sufficient to adjust the melting point of the molten salt mixture to a temperature of below about 500° F.

The molten salts, containing the higher and lower valent chlorides of a multivalent metal, can be employed in a wide variety of systems, and as a result, the present invention is applicable to a wide variety of processes. Thus, for example, molten salts employing the higher and lower valent chlorides of a multivalent metal can be employed for the production of chlorinated hydrocarbons. In such systems, the salt mixture containing the higher and lower valent chlorides of a multivalent metal can be contacted with a hydrocarbon either in the presence or absence of chlorine and/or hydrogen chloride, and the salt mixture may include or exclude the corresponding oxychloride. Such processes are described, for example, in U.S. Pat. Nos. 3,557,229, 3,879,480, 3,879,482, 3,865,886, U.S. Application Ser. No. 299,848 filed on Oct. 24, 1972 now abandoned; U.S. Application Ser. No. 299,114 filed on Oct. 19, 1972 now abandoned, all of which are hereby incorporated by reference. Similarly, molten salts containing the higher and lower valent chlorides of a multivalent metal have also been employed for dehydrogenation processes, as described, for example, in U.S. Pat. No. 3,637,895; for the production of alcohols, as described in U.S. Pat. No. 3,745,193; for dealkylation, as described in U.S. Pat. No. 3,536,773; for effecting coupling as described in U.S. Pat. No. 3,947,489; for oxidation as described in U.S. Pat. No. 3,641,157 and U.S. Pat. No. 3,947,489; for oxidation as described in U.S. Pat. No. 3,641,157 and U.S. Pat. No. 3,869,518; for the production of nitriles, as described in U.S. Pat. No. 3,865,238, all of which are hereby incorporated by reference. The molten salts are also employed for the production of chlorine, in which case chlorine is stripped from a molten salt mixture containing the higher and lower valent chlorides of a multivalent metal, resulting in a reduction in the higher valent contents of such a salt mixture. Such a process is described, for example, in U.S. Application Ser. No. 785,286 filed on Apr. 6, 1977 now U.S. Pat. No. 4,119,705, which is also hereby incorporated by reference.

The process of the present invention for separating volatized molten salts from an effluent stream may be employed in any one of the hereinabove noted processes; however, it is to be understood that the present invention is not limited to such processes.

The invention will be further described with respect to the drawings, which illustrate preferred embodiments of the present invention, wherein.

The present invention is being particularly described with respect to a molten salt reaction system employing the higher and lower valvent chlorides of a multivalent metal; however, the scope of the invention is not to be limited thereby. Similarly, although the embodiments are described with respect to the production of a chlorinated hydrocarbon, the scope of the invention is not limited to such production.

Figure 1:
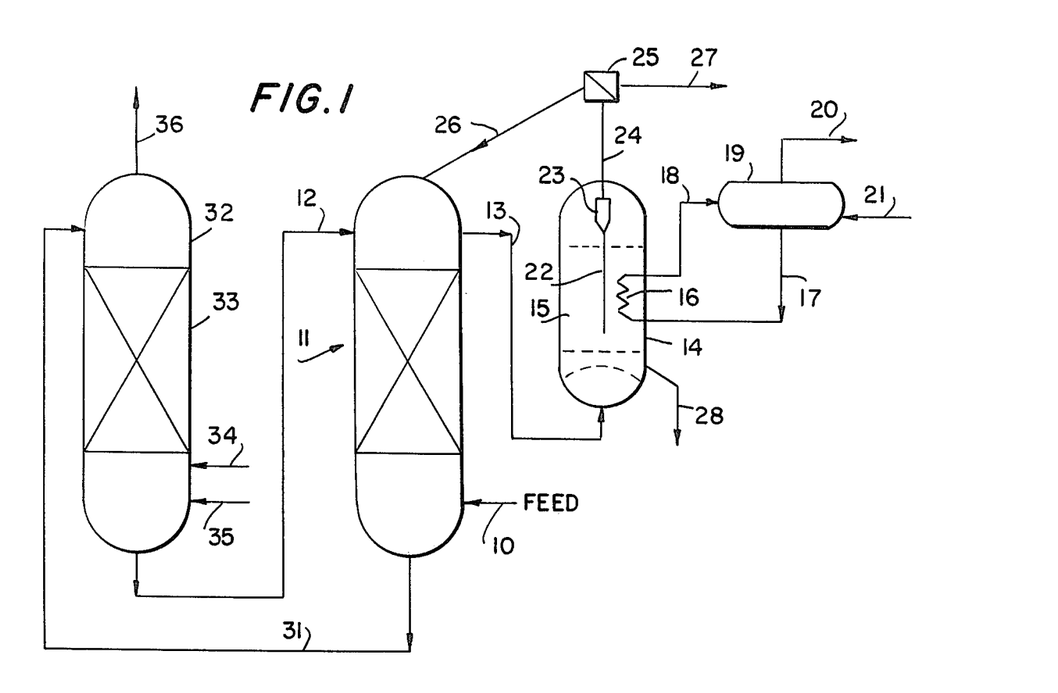
FIG. 1 is a simplified schematic flow diagram of one embodiment of the present invention.

Referring to FIG. 1, a hydrocarbon feed in line 10 is introduced into a chlorination reactor, schematically generally indicated as 11, wherein the hydrocarbon feed is contacted with a molten salt mixture containing the higher and lower valent chlorides of a multivalent metal, and preferably also a melting point depressant, such as a mixture of cuprous chloride, cupric chloride and potassium chloride, introduced into reactor 11 through line 12. As a result of the contact between the hydrocarbon and molten salt, chlorination is effected to produce chlorinated hydrocarbons.

A gaseous effluent, which includes a small amount of vaporized molten salt, is withdrawn from reactor 11 through line 13 and is introduced into a cooling vessel, schematically generally indicated as 14. The cooling vessel 14 contains a bed of solid particles, such as copper particles, with the bed schematically generally being indicated as 15. The bed is maintained in a fluidized state by introducing the gaseous effluent in line 13 at a superficial velocity to maintain such a fluidized state.

The bed 15 of solid particles is maintained at a temperature at which the vaporized salt present in the gaseous effluent in line 13 is condensed onto the bed of solid particles. For this purpose, the bed is provided with a cooling coil schematically generally indicated as 16, which is provided with a heat transfer fluid such as water. More particularly, water is introduced into the coil 16 through line 17 and as a result of the indirect heat transfer, steam is generated from the water in coil 16. A steam water mixture is withdrawn from coil 16 through line 18 and introduced into a vapor liquid separation tank, schematically generally indicated as 19. Steam is withdrawn from tank 19 through line 20, with water being withdrawn therefrom through line 17. Makeup water is introduced into tank 19 through line 21.

Gaseous effluent, free of voltatized salt is withdrawn from cooling tank 14 through line 22 which includes a cyclone separator 23 for removing entrained particles. As a result of the contact between the gaseous effluent and the fluidized solid particles in vessel 14, portions of the coated salt are attrited from the solid particles as fines, and such fines remain in the gaseous stream subsequent to passage through the cyclone separator 23. As a result, the gaseous effluent containing such fines in line 24 is introduced into a suitable solid separation device, such as filter 25 for separating such fines from the gaseous effluent. Such fines are returned to the reactor 11 through line 26. The gaseous effluent, now free of fines, is withdrawn from filter 25 through line 27 for further processing. As hereinabove noted, in some cases attrition of the condensed salt will reach equilibrium with deposition of the volatized molten salt from the gaseous effluent. In other cases, however, there will be a build up of condensed salt on the solid particles, and periodically, solid particles are withdrawn from vessel 14 through line 28 for further processing to remove such coated salt. In the case where such solid particles are copper, as particularly described, the copper particles containing condensed salt can be passed to the molten salt storage tank whereby the vaporized molten salt is returned to the system.

The molten salt withdrawn from reactor 11 through line 31 is introduced into an oxidation reactor schematically generally indicated as 32, including suitable gas liquid contacting means, schematically indicated as 33. In reactor 32, the molten salt is contacted with molecular oxygen introduced through line 34 and chlorine and/or hydrogen chloride introduced through line 35 to effect addition of chlorine values to the molten salt for subsequent use in reactor 11.

As hereinabove noted, alternatively, such chlorine values in the form of chlorine can be added to reactor 11 for effecting chlorination of the hydrocarbon in the presence of the molten salt.

As a further alternative, the oxidation reactor 32 may be operated in a manner such that the molten salt is withdrawn therefrom includes oxychloride whereby an oxychlorination reaction is effected in reactor 11.

As should be apparent, the overall invention is not limited to a specific processing scheme for employing the molten salts in that the process is generally applicable to a wide variety of processes employing molten salts in which the gaseous effluent contains volatized molten salt.

As hereinafter noted, the present embodiment is particularly suitable for removing volatized molten salt from a gaseous effluent in which oxygen is not present in reactor 11 either in gaseous form or in a chemically combined form such as the oxide or oxychloride, in that such effluents are free of water, and the process for separating volatized salt does not add water to the system.

A gaseous effluent is also withdrawn from reactor 32 through line 36, and if desired, volatized molten salt, if present in the effluent in line 36, can also be removed in accordance with the present invention.

Figure 2:
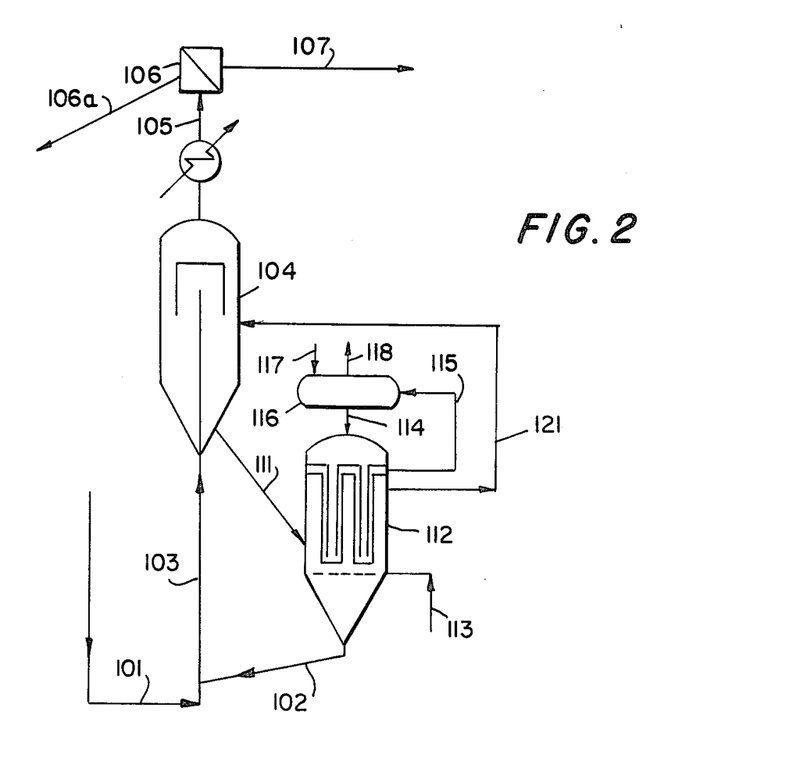
FIG. 2 is a simplified schematic flow diagram of another embodiment of the present invention.

Referring now to FIG. 2, which illustrates only the portion of the overall system employed for removing vaporized molten salt from the gaseous effluent, a gaseous effluent, as described with reference to FIG. 1, which includes a small amount of vaporized molten salt, in line 101, is contacted with solid particles introduced through line 102, which are at a temperature at which vaporized molten salt present in the gaseous effluent is condensed onto the solid particles. The solid particles and gaseous effluent flow through line 103 in a direct contact relationship, resulting in cooling of the gaseous effluent and condensation of vaporized molten salt onto the solid particles.

The mixture of gaseous effluent and solid particles are introduced into a gas-solid separator 104 to effect separation of the solid particles having condensed salt thereon from the gaseous effluent.

Gaseous effluent, free of volatized salt, and containing solid fines of the salt attrited from the solid particles is withdrawn from separator 104 through line 105 and introduced into a solid separation device, such as a filter 106 for separating such fines which may be recycled to the reaction system through line 106a.

The gaseous effluent, now free of fines, is withdrawn from filter 106 through line 107 for further processing.

Solid particles, having salt coated thereon, is withdrawn from separator 104 through line 111 and introduced into a cooling device 112 for reducing the temperature of the solid particles. As particularly shown, the solid particles are maintained as a fluidized bed in vessel 112 by a suitable fluidizing gas introduced through line 113. The fluidizing gas can be an appropriate recycle gas from the process.

In vessel 112, the solids are cooled in a fluidized state by indirect heat transfer with water introduced through line 114, with the water being converted to steam. A steam-water mixture is withdrawn from vessel 112 through line 115 and introduced into separator 116, which is provided with feed water through line 117. Steam is withdrawn through line 118 for processing use, with water being returned to vessel 112 through line 114 for generation of steam therefrom.

The cooled solids are withdrawn from vessel 112 through line 102 for effecting cooling of the gaseous effluent and condensing volatized salt.

The fluidizing gas is withdrawn from vessel 112 through line 121 and combined with the effluent gas in separator 104.

In accordance with the embodiment of FIG. 2, salt fines are preferably attrited from the solids in equilibrium with salt deposition, with such attrition occurring in the fluidized bed vessel 112, as well as during the contacting of the solids with the effluent gas. As a result, the fluidizing gas in line 121 includes solid salt fines, with such solid salt fines being ultimately recovered for recycle in filter 106.

It is to be understood that the fluidizing gas in line 113 may be a feed gas to the reaction system, either fresh feed or recycle feed, and as a modification of the embodiment of FIG. 2, the fluidizing gas, which contains attrited salt fines may be recycled to the reaction system to effect recycle of salt thereto directly from the fluidizing vessel 112. Thus, attrited salt fines are ultimately recycled to the reaction system in equilibrium with the deposition of such salt from the effluent gas onto the solid particles.

The embodiments of FIGS. 1 and 2 are particularly suitable for a reaction system in which the effluent gas is essentially free of water; however, it is to be understood that such embodiments could also be employed with an effluent gas which contains water.

Figure 3:
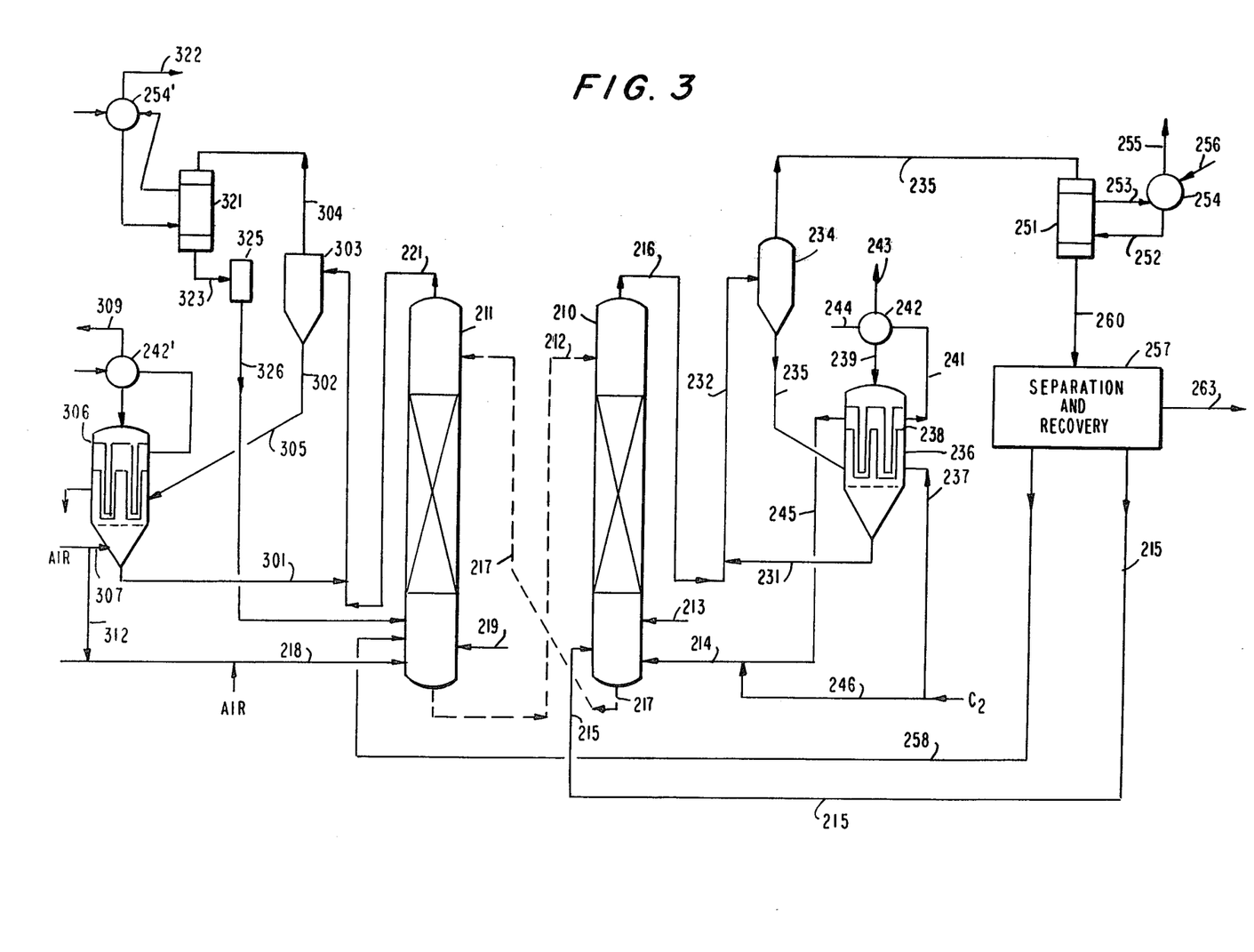
FIG. 3 is a simplified schematic flow diagram of a further embodiment of the present invention.

The embodiment of FIG. 3 is preferably employed for an effluent gas, which contains water.

Referring now to FIG. 3, there is shown a known reaction system for producing a chlorinated hydrocarbon by the use of molten salts, which includes a chlorination reactor 210 and an oxidation reactor 211. As known in the art, a molten salt mixture containing the higher and lower valent chlorides of a multivalent metal, and a melting point depressant, such as a molten salt mixture of cupric chloride, cuprous chloride, and potassium chloride, as a melting point depressant, and which further contains copper oxychloride, is introduced into the top of reactor 210 through line 212, wherein the molten salt is contacted with hydrogen chloride and/or chlorine introduced through line 213 and fresh feed hydrocarbon, such as ethane and/or ethylene introduced through line 214, as well as any recycle components, introduced through line 215. As a result of such countercurrent contact, the feed hydrocarbon is chlorinated to produce a chlorinated hydrocarbon effluent, which is withdrawn through line 216.

Molten salt is withdrawn from reactor 210 through line 217 and introduced into the oxidation reactor 211 wherein the molten salt countercurrently contacts a molecular oxygen containing gas, such as air, introduced through line 218 and wherein the salt may further contact recycle chlorine values introduced through line 219. As a result of the countercurrent contact, the salt is oxidized to generate the copper oxychloride, and any chlorine values are recovered as cupric chloride. The molten salt withdrawn from oxidation reactor 211 is then recirculated to reactor 210 through line 212.

A gas stream is withdrawn from reactor 211 through line 221.

The present invention will now be further described with respect to such known process for producing a chlorinated hydrocarbon by the use of molten salt.

The gaseous effluent withdrawn from reactor 210 through line 216 includes chlorinated hydrocarbons, some equilibrium amounts of hydrogen chloride, water vapor, some carbon dioxide and/or carbon monoxide, and vaporized salt.

The effluent in line 216 is contacted with solid particles; for example, sand, introduced through line 231, with such solid particles being at a temperature at which the vaporized salt present in the gaseous effluent is condensed onto the solid particles. The solid particles and effluent flow through line 232 in a direct contacting relationship, with line 232 functioning as a dilute phase transport contactor to effect cooling of the effluent and condensation of vaporized salt onto the solid particles.

The mixture of gaseous effluent and solid particles in line 232 are introduced into a gas solid separator 234 to effect separation of the solid particles having condensed salt thereon from the gaseous effluent.

Gaseous effluent essentially free of vaporized salt, and which may contain some fine particles of the solid salt which are attrited from the solid particles is withdrawn from the separator 234 through line 235 and treated as hereinafter described. A portion of the heat values present in the effluent are recovered from the effluent by the solid particles. Thus, for example, the reaction effluent in line 216 may be at a temperature in the order of from about 1000° F. to about 700° F., and such effluent is then cooled to a temperature in line 35 in the order of from about 450° F. to about 750° F. The cooling with the solid particles is to a temperature which is above the dew point of the water present in the effluent stream.

Heated solid particles, containing condensed salt, are withdrawn from separator 234 through line 235 and introduced into a heat recovery vessel, schematically generally indicated as 236. In vessel 236, heat is recovered from the solid particles while maintaining the solid particles in the vessel 236 as a fluidized bed. The particles are maintained in a fluidized state by a fluidizing gas introduced through line 237, with such fluidizing gas being a portion of the feed to be introduced into reactor 210. In particular, such fluidizing gas is a portion of the hydrocarbon feed; namely, ethane and/or ethylene to be introduced into reactor 210. It is to be understood, however, that other portions of the feed could also be employed. The fluidized bed of solid particles in vessel 236 is cooled to a temperature at which the solid particles can condense vaporized salt from the gaseous effluent in line 216. For this purpose, the bed is provided with a cooling coil, schematically generally indicated as 238, which is provided with a heat transfer fluid such as water. More particularly, water is introduced into the inlet portion of the cooling device through line 239, and as a result of the indirect heat transfer with the fluidized bed of solid particles, steam is generated from such water. A steam water mixture is withdrawn from the cooling device through line 241 and introduced into a vapor-liquid separation tank, schematically generally indicated as 242. Steam is withdrawn from tank 242 through line 243, with water being withdrawn therefrom through line 239. Makeup water may be introduced into the tank through line 244. In this manner, heat recovered from the gaseous effluent by the solid particles is recovered, with such recovery, as particularly described, being utilized for the generation of steam.

The fluidizing gas introduced through line 237 is heated by the solid particles. In addition, condensed salt is attrited from the solid particles, with the heated feed gas, including attrited salt fines being withdrawn from vessel 236 through line 245. Such heated feed gas, including the solid salt, is combined with the remainder of the net feed in line 246 for introduction into reactor 210 through line 214. As should be apparent, in this manner, a portion of the feed gas is preheated, while simultaneously being employed to recover potentially lost salt for recycle to the reaction system.

The effluent gas in line 235, which as hereinabove noted is essentially free of vaporized salt, and which may contain some solid salt particle fines attrited by the effluent gas, is passed through a heat exchange vessel, schematically generally indicated as 251 in order to recover further heat therefrom by indirect heat transfer with a suitable heat transfer liquid. In heat exchanger 251, as particularly described, water is introduced into the heat exchanger through line 252 with a steam-water mixture being withdrawn from the exchanger through line 253 for introduction into a liquid-gas separation vessel 254. Steam is withdrawn from vessel 254 through line 255 with the water being recycled to exchanger 251 through line 252. Makeup water may be introduced into vessel 254 through line 256.

In heat exchanger 251 the effluent gas is cooled to a temperature which is preferably above the dew temperature of water in order to prevent any condensation of water.

The further cooled effluent in line 260 is then introduced into a separation and recovery system, schematically generally indicated as 257. In the separation and recovery system, remaining salt fines are separated from the effluent for recovery and recycle to the reaction system. In addition, various reaction products and recycle components are separated, with such separation and recovery being effected by procedures generally known in the art.

In accordance with a preferred embodiment, any solid salts present in the effluent may be recovered from the effluent during the procedure for condensing process generated water from the effluent, generally as a dilute aqueous hydrogen chloride solution. Thus, for example, the effluent may be directly contacted in a quench cooling tower, including suitable packing, with a cooled dilute aqueous hydrogen chloride stream to condense process water therefrom, as dilute aqueous hydrogen chloride, with such dilute aqueous hydrogen chloride also including dissolved salt fines. Condensed aqueous hydrogen chloride, including dissolved salt fines, may be recycled to the reaction system through line 258 in particular, to the oxidation reactor 211.

Net reaction product is recovered from separation recovery zone 257 through line 263 and recycle components, if any, are recovered through line 215.

Thus, in accordance with the present invention, heat is effectively recovered from the effluent in line 216, while simultaneously providing for recovery and recycle of volatized salt contained therein.

Referring back to oxidation reactor 211, the effluent in line 221 also includes small amounts of vaporized salt, and also should be subjected to a heat recovery operation. Such gaseous reaction effluent is treated in a manner similar to the effluent in line 216, and as a result, the description of such treatment will be described in less detail.

Thus, the effluent in line 221 is contacted with solid particles in line 301, with the solid particles being at a temperature sufficient to cool the effluent gas and condense vaporized salt onto the solid particles. The combined stream is passed through line 302, which functions as a dilute phase transport cooling contactor. The solid gas mixture in line 302 is introduced into a gas-solid separator 303 to separate heated particles, containing condensed salt, from the gas. The gaseous effluent, now free of volatized salt, and containing some amounts of solid salt fines, as a result of attrition, is withdrawn from separator 303 through line 304.

The heated particles, containing condensed salt, are withdrawn from separator 303 through line 305 and introduced into a cooling vessel, schematically generally indicated as 306. In vessel 306, the solid particles are cooled as a fluidized bed. The solid particles are maintained as a fluidized bed by a fluidizing gas introduced through line 307, with such fluidizing gas being a portion of the feed to be introduced into oxidizer 211; in particular, an oxygen containing gas such as air. The solid particles are cooled as a fluidized bed in vessel 306 by indirect heat transfer with a suitable heat transfer liquid. As particularly shown, as described with reference to vessel 236, such indirect heat transfer fluid may be water to generate steam. Such steam is recovered through line 309. Thus, a portion of the heat of the effluent is recovered by the solid particles, with such heat ultimately being employed to generate steam.

The fluidizing gas introduced through line 307; namely, air, is heated by the solid particles. In addition, condensed salt is attrited from the solid particles, with the heated fluidizing gas, containing attrited salt fines, being withdrawn from vessel 306 through line 311. Such gas is combined with the remaining portion of the air feed in line 312 for introduction into oxidation vessel 211 through line 218.

The gaseous effluent in line 304 is further passed through heat exchanger 321 to recover further heat therefrom by indirect heat transfer. In heat exchanger 321, the effluent is cooled to a temperature which is preferably above the dew point of water contained in the effluent. Such cooling in vessel 321 is generally effected by the use of an indirect heat transfer liquid, such as water, which can be used to generate steam recovered through line 322. The liquid gas separation vessel 254' can be the same vessel as used in the chlorination section. This is also the case as for vessel 242'.

The cooled effluent in line 323 is then introduced into a further treating zone, schematically generally indicated as 325 for further processing as known in the art. Thus, for example, such effluent may be further cooled in a direct contact quench tower to recover aqueous hydrogen chloride, with any salt fines present in the effluent being recovered with the aqueous hydrogen chloride. Such aqueous hydrogen chloride can be recycled to the oxidizer through line 326 as known in the art. Although such an embodiment is preferred, it is to be understood that other means for recovering the salt fines can also be employed.

Thus, in accordance with the present invention, heat and volatized salt are also effectively recovered from the oxidation reaction effluent.

The embodiment of FIG. 3 may be modified within the spirit and scope of the invention. Thus, for example, it is possible to use a portion of the feed to either the oxidizer and/or the chlorination vessel in both of the cooling vessels as a fluidizing gas. Thus, the embodiment of FIG. 3 is not limited to the particularly described scheme wherein the fluidized cooling bed for the chlorination reactor is fluidized by a feed gas to the chlorination reactor and the fluidized cooling bed for the oxidation reactor is fluidized by a feed gas to the oxidation reactor. Such fluidization of either or both of the vessels may be accomplished by any one of the feed gases to the system in that such an expedient would result in preheating of the feed gas and effective recovery and recycle of solid salt. It is to be understood that the term feed gas encompasses fresh feed to the system as well as one or more recycle components employed as recyle feed to the system.

Furthermore, although cooling of the effluent gas in an exchanger is preferably to a temperature which is above the dew point of water to present condensation of corrosive liquid (dilute aqueous hydrogen chloride), it is to be understood that cooling could be to below the dew point of water; however, such an expedient may necessitate the use of special construction materials for the exchanger as a result of potential corrosion problems.

In some cases, there may be some condensation of heavy organics in the exchanger and in the event that such heavy organics have a tendency to adhere to exchanger surfaces, some liquid organics may be recycled through the exchanger along with the effluent to wash such exchanger surfaces.

In addition, although the invention has been particularly described with respect to a specific type of molten salt system, the teachings of the invention are equally applicable to other molten salt systems. In addition, the teachings of the invention are also applicable to systems employing salts other than in molten form wherein vaporized salt is present in the effluent and it is also necessary to recover heat from such effluent.

The present invention is particularly advantageous in that it is possible to effectively recover heat from a reaction system to save energy, while simultaneously recovering and recycling salt present as vapor in the effluent streams. Thus, for example, in accordance with FIG. 3, in a plant capable of producing 500 MM pounds per year of vinyl chloride, the chlorination reactor effluent would contain, for example, about 16 lbs. per hour of molten salt vapor and such an effluent would have a water dew point of about 240° F. The effluent from the oxidation reactor would contain about 8 lbs. per hour of salt and would have a water dew point of 172° F. In such an embodiment, the gaseous effluents in lines 216 and 221 are each cooled to a temperature of about 650° F. by circulating sand or copper, with such solid particles being cooled in each of coolers 306 and 236 to a temperature of about 550° F. Fluidization in vessel 236 could be accomplished with about 685 Mols per hour of ethane feed to the plant, which comprises about 60% of the feed, and fluidization in vessel 306 could be accomplished with about 350 Mols per hour of air, which is about 25% of the air feed. Both the ethane and the air are heated to a temperature of about 550° F. in the fluidized bed coolers, which results in a heat input of about 7.5 MM BTU/HR of heat input into the system.

The effluents in lines 235 and 304 are each cooled to about 400° F. in the heat exchangers 251 and 321 respectively. In such a system, 28,700 lbs. per hour of 180 psig steam is generated in cooling vessel 236 and 14,900 lbs. per hour of 180 psig steam is generated in cooling vessel 306. In addition, heat exchanger 251 generates 41,500 lbs. per hour of 75 psig steam and heat exchanger 321 generates 21,000 per hour of 75 psig steam.

Numerous modifications and variations of the present invention are possible in light of the above teachings, and therefore, within the scope of the appended claims, the invention may be practised otherwise than as particularly described.

I claim:

1. A process for recovering vaporized salt from a gaseous reaction effluent withdrawn from a reaction system employing the salt while simultaneously recovering heat from the reaction effluent, comprising:
    contacting the gaseous reaction effluent with solid particles by suspending the solid particles in flowing gaseous reaction effluent to provide dilute phase transport contact, said solid particles being at a temperature at which vaporized salt condenses from the gas onto the solid particles, said solid particles being heated and said gaseous reaction effluent being cooled by said contact;
    separating gaseous reaction effluent from the solid particles;
    cooling separated solid particles in a fluidized bed, said fluidized bed being fluidized by a fluidizing gas, said particles being cooled in the fluidized bed to a temperature at which vaporized salt condenses onto the solid particles;
    employing cooled solid particles for contacting the gaseous reaction effluent; and
    recovering and recycling to the reaction system solid salt fines attrited from the solid particles and present in the fluidizing and reaction effluent gases, said solid salt fines being attrited in equilibrium with the condensation of vaporized salt onto the solid particles.

2. The process of claim 1 wherein the fluidizing gas is a feed gas to the reaction system and solid salt fines are recovered and recycled to the reaction system in the fluidizing gas.

3. The process of claim 1 wherein the salt is employed in the reaction system in molten form.

4. The process of claim 1 wherein the solid particles are cooled in the fluidized bed by indirect heat transfer.

5. The process of claim 1 wherein the effluent gas from the reaction system is essentially free of water.

6. The process of claim 1 wherein solid salt fines are recovered from the fluidizing and reaction effluent gases by filtration.

7. A process for recovering heat from a reaction effluent containing a volatized salt, comprising:
    withdrawing from a reaction system an effluent containing vaporized salt;
    contacting the effluent with solid particles in a dilute phase transport contact zone, said solid particles being at a temperature at which vaporized salt condenses from the gas onto the solid particles, said solid particles cooling the effluent gas;

separating the solid particles containing condensed salt from the effluent gas;

further cooling the effluent gas by indirect heat transfer to recover further heat therefrom;

introducing separated solid particles containing condensed salt into a cooling zone wherein the particles are maintained as a fluidized bed by at least a portion of a feed gas to the reaction system, said fluidizing gas being heated by the particles and partially cooling the particles, with solid salt fines being attrited from the particles by the feed gas, said particles also being cooled in the fluidized bed by indirect heat transfer to recover heat from the solid particles;

employing cooled solid particles for contacting the effluent gas; and passing heated feed gas, containing attrited salt fines, from the cooling zone to the reaction system.

8. The process of claim 7 wherein the fluidized bed of particles is cooled by indirect heat transfer with water to generate steam.

9. The process of claim 8 wherein the further cooled effluent gas includes attrited salt fines which are recovered therefrom and recycled to the reaction system.

10. The process of claim 9 wherein the effluent gas includes water vapor and the further cooling of the gas is to a temperature which is above the dew point of water in the effluent gas.

11. The process of claim 10 wherein the effluent gas is further cooled by indirect heat transfer with water to produce steam.

12. The process of claim 10 wherein volatized salt is derived from molten salt employed in the reaction system.

13. The process of claim 7 wherein solid salt fines are attrited from the solid particles by the fluidizing gas and the effluent gas in equilibrium with salt condensation onto the solid particles.

14. In a system for producing a chlorinated hydrocarbon wherein a molten salt containing the higher and lower valent chlorides of a multivalent metal is oxidized in a first reaction zone and molten salt from the first reaction zone is employed in a second reaction zone for producing chlorinated hydrocarbon, and wherein effluent gas withdrawn from the second reaction zone includes volatized salt, the improvement for recovering heat from the effluent gas, comprising:

contacting the effluent gas with solid particles in a dilute phase transport contact zone, said solid particles being at a temperature at which vaporized salt condenses from the gas onto the solid particles, said solid particles cooling the effluent gas;

separating the solid particles containing condensed salt from the effluent gas;

further cooling the effluent gas by indirect heat transfer to recover further heat therefrom;

introducing separated solid particles containing condensed salt into a cooling zone wherein the particles are maintained as a fluidized bed by at least a portion of a feed gas to one of the first and second reaction zones, said fluidizing gas being heated by the particles and partially cooling the particles, with solid salt fines being attrited from the particles by the feed gas, said fluidized bed of particles also being cooled by indirect heat transfer to recover heat therefrom;

employing cooled solid particles for contacting the effluent gas; and passing heated feed gas, containing attrited salt fines, to one of the first and second reaction zones.

15. The process of claim 14 wherein the effluent gas includes water vapor and some hydrogen chloride, said further cooling of the effluent being to a temperature above the dew point of water in the effluent gas.

16. The process of claim 15 wherein the further cooled effluent gas includes attrited salt fines, and aqueous hydrogen chloride is condensed therefrom, said condensed aqueous hydrogen chloride including dissolved salt fines being recycled to the first reaction zone.

17. The process of claim 16 wherein the fluidized bed of particles is cooled by indirect heat transfer with water to generate steam.

18. The process of claim 17 wherein the effluent gas is further cooled by indirect heat transfer with water to produce steam.

19. The process of claim 14 wherein the molten salt contains cuprous and cupric chloride.

20. The process of claim 14 wherein solid salt fines are attrited from the solid particles by the fluidizing gas and the effluent gas in equilibrium with salt condensation onto the solid particles.

21. The process of claim 14 wherein the fluidizing gas is a feed to the second reaction zone.

22. The process of claim 14 wherein an oxidation effluent gas, containing vaporized salt, is withdrawn from the first reaction zone, and further comprising;

contacting the oxidation effluent gas with solid particles in a dilute phase transport contact zone, said solid particles being at a temperature at which vaporized salt condenses from the oxidation effluent gas onto the solid particles, said solid particles cooling the oxidation effluent gas;

separating the solid particles containing condensed salt from the oxidation effluent gas;

further cooling the oxidation effluent gas by indirect heat transfer to recover further heat therefrom;

introducing separated solid particles, containing condensed salt, into a cooling zone wherein the particles are maintained as a fluidized bed by at least a portion of a feed gas to the first reaction zone, said fluidizing gas being heated by the particles and partially cooling the solids, with solid salt fines being attrited from the particles by the feed gas, said fluidized bed of particles also being cooled by indirect heat transfer to recover heat therefrom;

employing cooled solid particles for contacting the oxidation effluent gas; and passing heated feed gas, containing attrited salt fines from the cooling zone to the first reaction zone.

23. A process for recovering vaporized molten salt from a gas produced in a reaction zone employing a molten salt mixture containing cuprous and cupric chloride, comprising:

(a) withdrawing from the reaction zone a gas containing reaction product and vaporized molten salt, as an impurity, said vaporized molten salt comprising cuprous and cupric chloride;

(b) contacting said gas with solid particles, said solid particles being at a temperature at which vaporized molten salt condenses from the gas onto the solid particles, said gas contacting also attriting solid fines of cuprous and cupric chloride from the solids in equilibrium with the condensation;

(c) separating said gas, containing solid fines from the solid particles;

(d) separating solid fines from the gas;

(e) recycling solid fines to the reaction zone;

(f) cooling said solid particles to maintain said solid particles at a temperature at which vaporized molten salt condenses from the gas; and (g) employing cooled solid particles in step (b).

24. The process of claim 23 wherein said gas is contacted with said solid particles with the solid particles being employed as a fluidized bed, said solid particles being cooled in said fluidized bed by indirect heat transfer with a heat transfer fluid to thereby recover heat while effecting said cooling.

25. The process of claim 24 wherein said gas withdrawn from the reaction zone is essentially free of water.

26. A process for recovering vaporized molten salt from a gas produced in a reaction zone employing a molten salt mixture containing cuprous and cupric chloride, comprising:

(a) withdrawing from the reaction zone a gas containing reaction product and vaporized molten salt, as an impurity, said vaporized molten salt comprising cuprous and cupric chloride;

(b) contacting said gas with solid particles comprised of at least one member selected from the group consisting of copper, cuprous chloride and cupric chloride by suspending the solid particles in the gas, said solid particles being at a temperature at which vaporized molten salt condenses from the gas onto the solid particles;

(c) separating said gas from the solid particles;

(d) cooling said separated solid particles in a fluidized bed to maintain said solid particles at a temperature at which vaporized molten salt condenses from the gas, said cooling being effected by indirect heat transfer with a heat transfer fluid for heat recovery;

(e) employing cooled solid particles from the fluidized bed in step (b); and (f) periodically introducing solid particles containing condensed salt into the reaction zone.

27. The process of claim 26 wherein said gas withdrawn from the reaction zone is essentially free of water.

* * * * *